United States Patent
Amann et al.

(10) Patent No.: US 10,314,643 B2
(45) Date of Patent: Jun. 11, 2019

(54) INSTRUMENT FOR SEALING VESSELS

(71) Applicant: Erbe Elektromedizin GmbH, Tuebingen (DE)

(72) Inventors: Marcus Amann, Tuebingen (DE); Daniel Schaeller, Tuebingen (DE); Volker Mayer, Tuebingen (DE); Martina Düppuis, Pliezhausen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 603 days.

(21) Appl. No.: 14/482,224

(22) Filed: Sep. 10, 2014

(65) Prior Publication Data
US 2015/0073408 A1    Mar. 12, 2015

(30) Foreign Application Priority Data

Sep. 10, 2013 (EP) .................................. 13183641
Sep. 12, 2013 (EP) .................................. 13184185

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/1455* (2013.01); *Y10T 29/49117* (2015.01)

(58) Field of Classification Search
CPC ........ A61B 18/1445; A61B 2018/0063; A61B 2018/1455; A61B 18/1442;
(Continued)

(56) References Cited

U.S. PATENT DOCUMENTS 8,668,691 B2    3/2014  Heard
8,939,975 B2 *  1/2015  Twomey ............ A61B 18/1442
                                                    606/52
(Continued)

FOREIGN PATENT DOCUMENTS

CN    102525639 A    7/2012
CN    202313713 U    7/2012
(Continued)

OTHER PUBLICATIONS

Office action and Search report in corresponding Chinese Application No. 201410457145.4, dated Feb. 26, 2016, 15 pages.
(Continued)

*Primary Examiner* — Jaymi E Della
(74) *Attorney, Agent, or Firm* — Fitch, Even, Tabin & Flannery LLP

(57) ABSTRACT

A surgical instrument 10 suitable for sealing tissue includes a tool 15 with at least one branch 16 comprising an electrode unit 35, which consists of a sheet metal part 35. The part 35 is anchored in a positive manner in a plastic body 34. Strip sections 40, 41 of the metal part 35 extend into the plastic body 34, encompassing openings 42, 42 or slits 43, 43a, through which the plastic body 34 extends. A positive anchoring of the sheet metal part 35 in the plastic body 34 and minimizing of the heat introduction into the plastic body 34 is thus attained. The thermal capacity of the sheet metal part 35 and the thermal conductivity of the plastic body 34 are low, so that consistently positive coagulation results are reached even after repeated use in short succession, regardless of the initial temperature of the tissue contact surfaces 36.

12 Claims, 6 Drawing Sheets

(58) Field of Classification Search
 CPC .......... A61B 2018/00601; A61B 17/28; A61B
 2017/2804; A61B 2017/2808; A61B
 17/2812; A61B 17/282; A61B 2017/2825;
 A61B 17/29; A61B 2017/2926; A61B
 2017/2927; A61B 2017/2929; A61B
 2017/2931; A61B 2017/2943; A61B
 2017/2944; A61B 2017/2945; A61B
 2017/2948; A61B 18/085
 See application file for complete search history.

(56) References Cited

U.S. PATENT DOCUMENTS

| | | | |
|---|---|---|---|
| 2004/0122423 A1 | 6/2004 | Dycus et al. | |
| 2009/0082769 A1* | 3/2009 | Unger | A61B 18/1445 606/52 |
| 2011/0066150 A1 | 3/2011 | Beller | |
| 2011/0073246 A1* | 3/2011 | Brandt | A61B 18/1445 156/242 |
| 2011/0245825 A1 | 10/2011 | Mitzlaff et al. | |
| 2012/0083784 A1* | 4/2012 | Davison | A61B 18/1445 606/48 |
| 2012/0083786 A1 | 4/2012 | Artale et al. | |
| 2012/0172873 A1* | 7/2012 | Artale | A61B 18/1442 606/46 |
| 2012/0215220 A1* | 8/2012 | Manzo | A61B 18/1445 606/46 |
| 2013/0018372 A1 | 1/2013 | Sims et al. | |
| 2013/0046295 A1 | 2/2013 | Kerr et al. | |
| 2013/0046306 A1 | 2/2013 | Evans et al. | |
| 2013/0071282 A1 | 3/2013 | Fry | |
| 2013/0185922 A1 | 7/2013 | Twomey et al. | |
| 2013/0218198 A1 | 8/2013 | Larson et al. | |

FOREIGN PATENT DOCUMENTS

| | | |
|---|---|---|
| EP | 2371316 A1 | 10/2011 |
| EP | 2377480 A1 | 10/2011 |
| JP | 2004532676 A | 10/2004 |
| JP | 2010253278 A | 11/2010 |
| JP | 2011517608 A | 6/2011 |
| JP | 2012075906 A | 4/2012 |
| WO | 02/080785 A1 | 10/2002 |

OTHER PUBLICATIONS

Search Report in corresponding Japanese Application No. 2014-184603, dated Sep. 15, 2015, 34 pages.
Japanese Office action in corresponding Japanese Application No. 2014-184603, dated May 24, 2016, 6 pages.
European Search Report in corresponding European Application No. EP13184185.0 dated Jan. 8, 2014, 7 pages.
European Extended Search Report in corresponding European Application No. EP13184185.0 dated Jun. 2, 2014, 12 pages.
Notice of Reasons for Refusal in corresponding Japanese Application No. 2014-184603, dated Sep. 29, 2015, 6 pages.
Notice of Preliminary Rejection in corresponding Korean Application No. 2014-0117526, dated Oct. 21, 2015, 13 pages.
Second office action in corresponding Chinese application No. 201410457145.4, dated Sep. 28, 2016, 14 pages.

* cited by examiner

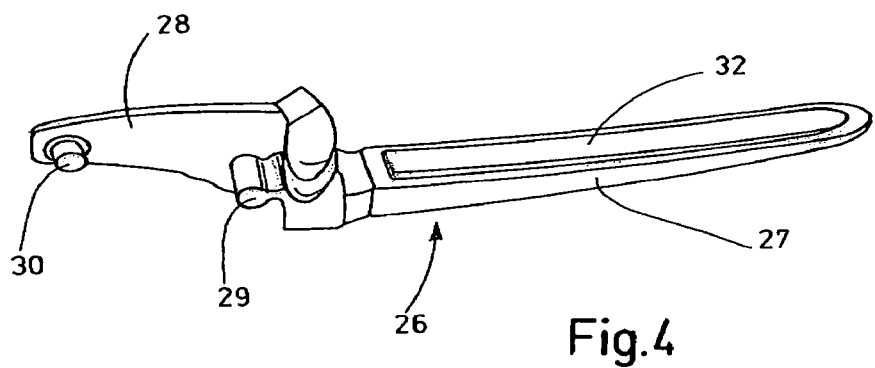
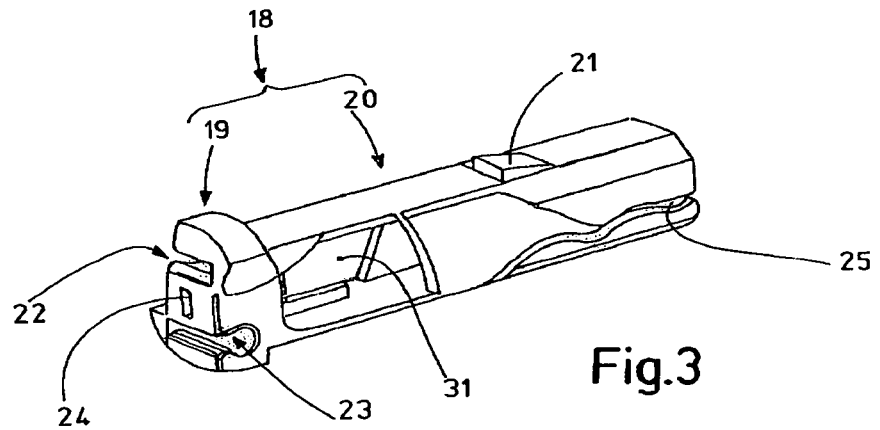

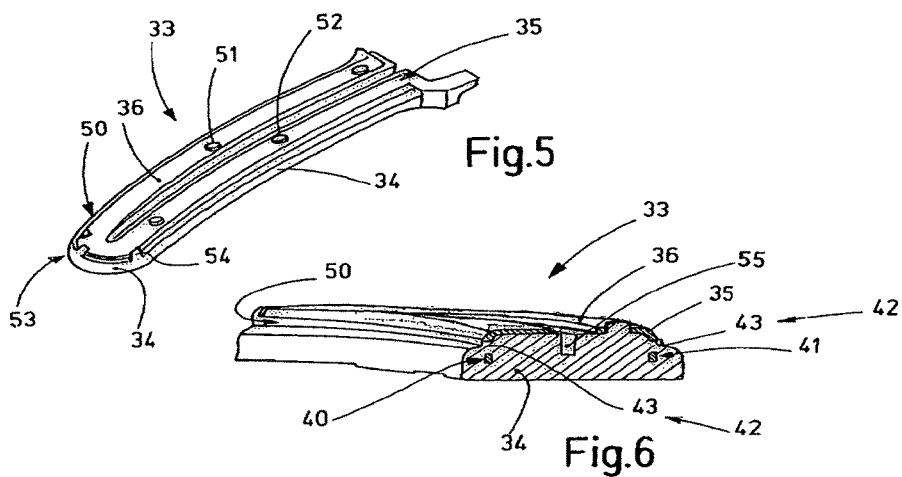
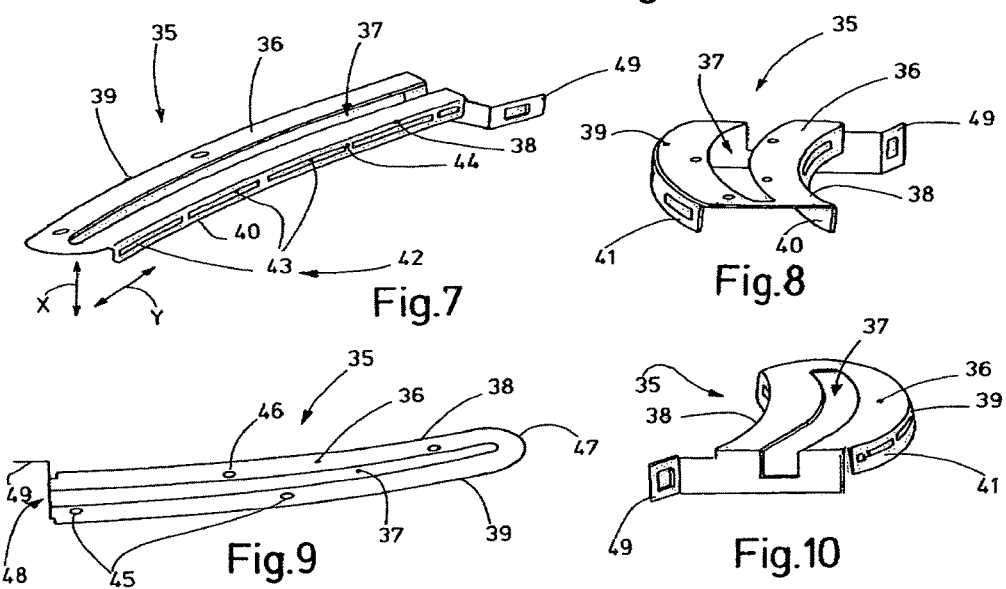

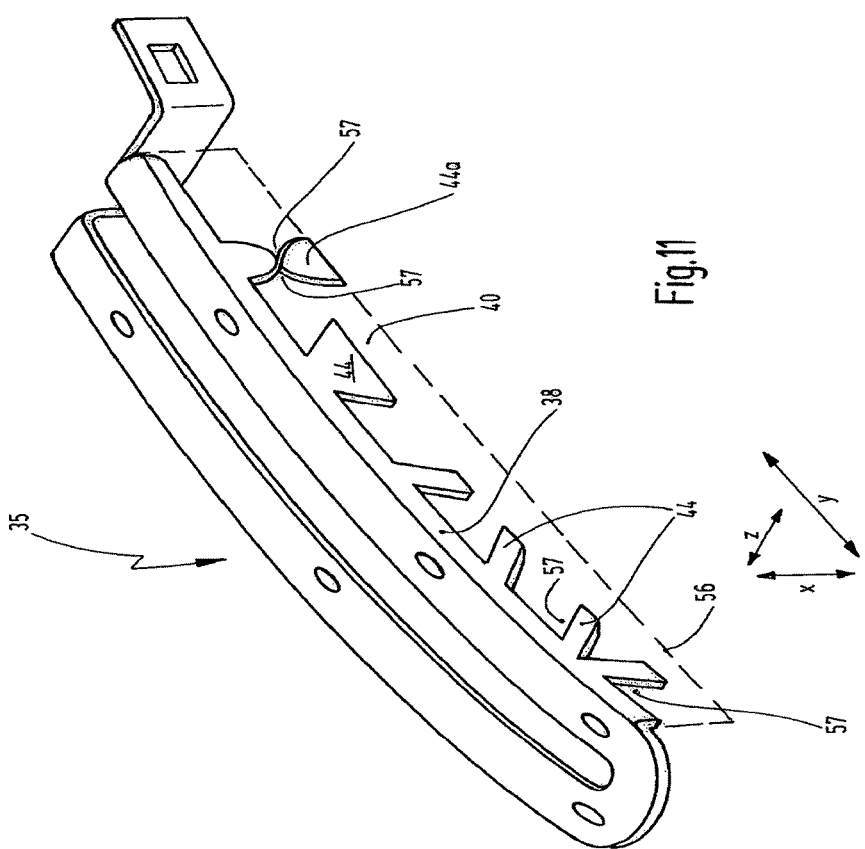

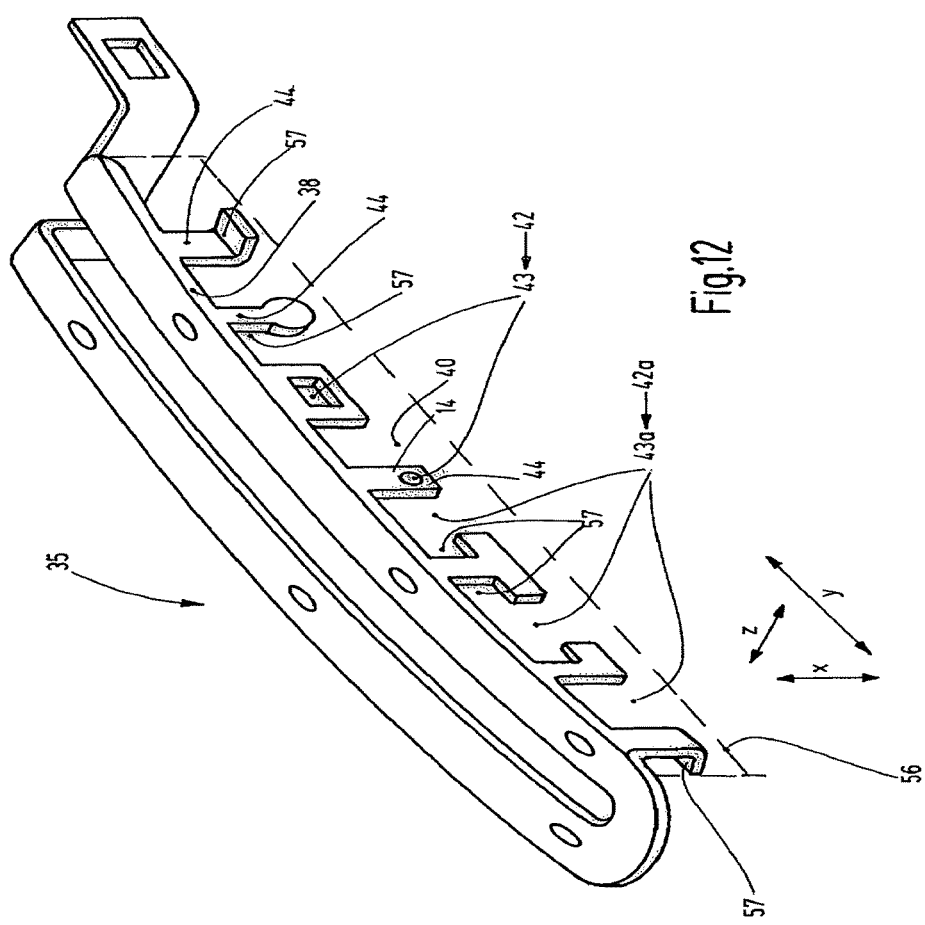

INSTRUMENT FOR SEALING VESSELS

RELATED APPLICATION(S)

This application claims the benefit of European Patent Application No. EP13183641.3 filed Sep. 10, 2013 and European Patent Application No. EP 13184185.0 filed Sep. 12, 2013, the contents of each of which are incorporated herein by reference as if fully rewritten herein.

TECHNICAL FIELD

The invention relates to a surgical instrument for coagulating tissue, in particular for sealing vessels. For example, such instruments can be used for sealing, fusing and coagulating tissue, for example blood vessels. Provision can be made for severing the tissue after coagulation as well.

BACKGROUND

Hereinbelow, the term "distal" always describes the part of the instrument or component, which is spaced apart from the user, the term "proximal" always describes the closer part of the instrument or component, which is oriented towards the user.

Instruments of the mentioned design are known on principle. For example, EP 2371316 A1 discloses such an instrument comprising an elongated shaft, which is held at its proximal end at a housing, from which it extends away. A handle and an operating lever are embodied at the housing approximately at a right angle to the shaft. A forcipate tool comprising two branches, which are also identified as jaw parts, is arranged at the distal end of the shaft. While one of the jaw parts is arranged so as to be fixed, the other jaw part can be moved towards and away from the fixed jaw part. To move said jaw part, it is connected to the operating lever via pulling devices and a drive.

The jaw parts can be energized during the use, so as to heat a biological tissue, which is seized between the jaw parts, for example a blood vessel, by means of current flow. In addition, the tool can comprise a blade, so as to be able to sever a vessel, which is seized and fused between the branches.

Such instruments are used both as instruments, which can be sterilized, as well as disposable instruments. In the case of disposable instruments, a simple and cost-efficient design is important, whereby, however, compromises with regard to the functionality are not desired. In the case of reusable instruments, the ability to easily clean and sterilize and the robustness against high temperatures or other sterilizing effects is important. Comprises with regard to the functionality are also not desired or acceptable, respectively, herein.

SUMMARY

Based on this, it is the object of the invention to create an instrument comprising a simple and robust design as well as comprising a high functionality.

The instrument according to the invention encompasses a tool comprising at least one movable branch, which comprises a branch support and an electrode unit. The electrode unit consists of a sheet metal part, which is preferably produced as stamped-bent part, which is partly embedded in a plastic body and is anchored therein. At two long edges, the sheet metal part encompasses strip sections for this purpose, which are angled relative to the tissue contact surfaces. These strip sections extend into the plastic body, which thus fills the space between the strip sections, envelopes the strip sections and preferably leaves open the tissue contact surfaces.

The strip sections are provided with openings, through which the plastic body extends, and thus forms a positive connection to the sheet metal part. The plastic body can be produced by insert molding the sheet metal part or its angled strip sections, respectively. The sheet metal part, which is insert molded with the plastic, forms the electrode unit.

Preferably, the openings in the strip sections are embodied so as to have a large surface. They can be formed by means of round holes, angular holes or, as is preferred, by means of slits. This design provides for a simple and efficient production. This is advantageous for the use of the surgical instrument as disposal instrument.

In response to the use of the instrument, the proposed concept leads to a thermal stress of the plastic, which is influenced by the shape and the design of the sheet metal part. Due to their openings, the strip sections, which extend into the plastic, can only introduce limited heat quantities into the plastic body in this area. The openings, which are provided in the strip sections, thus interrupt and limit the heat flow from the tissue contact surfaces into the edge area of the plastic body. As a result, the tissue, which rests against the plastic body in this edge area, experiences less desirable thermal damages.

The design of the electrode unit according to the invention furthermore leads to well-reproducible coagulation results. The thermal capacity of the sheet metal part and the thermal conductivity of the plastic body are relatively low. The tissue contact surface, together with the biological tissue, can thus heat up to the desired tissue temperature in a highly dynamic manner and without large delays during the use. This accommodates the handling safety and a reduced treatment time. The user obtains virtually uniform coagulation or sealing results, respectively, regardless of whether he uses a cold instrument, which has not yet been used, or an instrument, by means of which he already carried out one or a plurality of coagulations or sealings, respectively, shortly beforehand, and the tissue contact surfaces of which have an increased initial temperature.

A further advantage of the embedding of thin sheet metal parts, which are provided as electrodes or tissue contact surfaces, respectively, into the plastic body, lies in the thermal and electric insulation of the sheet metal part against surrounding tissue. Undesirable coagulation effects are thus minimized in the vicinity of the surgical site.

The electrode unit, which belongs to the instrument according to the invention, can be supported by branch supports made of plastic as well as by branch supports made of metal. The latter is preferred. In particular the electrical insulation of the sheet metal part from the respective supporting branch support by the plastic body is thereby advantageous. Branch supports, which consist of metal, are uncoupled electrically from the tissue contact surfaces and are only impacted slightly by the electrode units and thus do not lead to effects in the surrounding tissue. This also provides the user with the possibility of sealing vessels under more difficult conditions, for example in the case of limited access to the tissue, which is to be treated.

If webs, the width of which is not larger than the length thereof, are arranged between the openings, which are embodied in the strip sections, the heat flow starting at these strip sections into the plastic body is noticeably. This applies in particular, if the surface of the openings is larger than the surface of the webs, which are present between the openings. It is considered to be advantageous in particular, if the ratio of the surfaces of the openings to the surface of the webs is as large as possible and lies within the range of between 3 to 1 and 20 to 1, preferably 10 to 1.

Preferably, the plastic body is embodied such that it encompasses an insulating area laterally next to the tissue contact surface. This area can be embodied as step or as a shoulder, which is shaped in a different manner, for example in the shape of a bevel. This leads to a sufficient distance between the tissue contact surfaces and surrounding tissue, which is not to be impacted.

The tissue contact surface is preferably interrupted by means of a longitudinal slit. A longitudinally movable blade can be guided in said slit. In the case of this design, provision is preferably made in the plastic body in an aligned orientation to the longitudinal slit for a blade guide groove. The latter is preferably narrower than the longitudinal slit. The blade is thus electrically insulated from the sheet metal part. Electrical short-circuits between the tissue contact surfaces of the two branches and the blade are avoided through this.

As mentioned, the sheet metal part can be formed as stamped-bent part. It can also be produced in a different manner, for example by means of laser machining, water jet technology or chemically by means of etching or other methods. Preferably, one or a plurality of recesses, for example in the shape of boreholes, through which the elastic body extends so as to form holding means, are embodied in the tissue contact surface. In this manner, an electrical short-circuit can be avoided between the two sheet metal parts in response to the closing of the branches and the fixation of the seized tissue can be improved during the sealing process. The holdings means can be offset against one another on both sides of the blade slit or can be arranged symmetrically. The holding means can also be arranged so as to be offset relative to the branches located opposite thereto, so that the holding means do not meet one another in response to the closing of the branches, but can touch the opposite tissue contact surface. The holding means clamp the tissue, which shrinks during the sealing process, whereby the quality of the sealing is increased. In addition, these holding means can also serve as spacers between the tissue contact surfaces.

The extensive expansion of the individual holding means influences the sealing result and the holding of the clamped tissue. This is why it is advantageous, if the surface areas of the individual holding means lie in a range of between 0.5 mm$^2$ and 7 mm$^2$, preferably 1 mm$^2$, more preferably 0.75 mm$^2$.

To prevent the electrical contact between the tissue contact surfaces of the branches, spacers are preferably arranged at the edge of the tissue contact surfaces of the sheet metal parts, in particular at the distal end. Said spacers can be formed by means of projections of the plastic body, which project beyond the tissue contact surface.

In the case of each of the afore-mentioned instruments, the two electrode units can be fastened to branch supports made of metal. In addition, the branches can be movably supported in the case of each of the afore-mentioned instruments.

The two electrode units are preferably fastened to movably supported branch supports. The branch supports can be in electrical contact with one another such that they lie on a uniform electrical potential, which is preferably floating and thus not electrically contacted. This also serves to minimize undesired effects on surrounding tissue.

Further details of advantageous embodiments of the invention are the subject matter of claims, the drawings or the description.

BRIEF DESCRIPTION OF THE DRAWINGS

FIG. 3 shows a base part for accommodating and supporting two branches, FIG. 4 shows a branch support for accommodating the electrode unit, FIG. 5 shows the electrode unit of a branch of the tool according to FIG. 2, in perspective illustration, FIG. 6 shows the electrode unit according to FIG. 5 in perspective sectional illustration, FIGS. 7-10 show a sheet metal part for the set-up of the electrode unit according to FIGS. 5 and 6, in various views, and FIGS. 11 and 12 show a sheet metal part for the set-up of the electrode unit according to FIGS. 5 and 6 comprising various embodiments of the strip sections.

DETAILED DESCRIPTION

Figure 1:
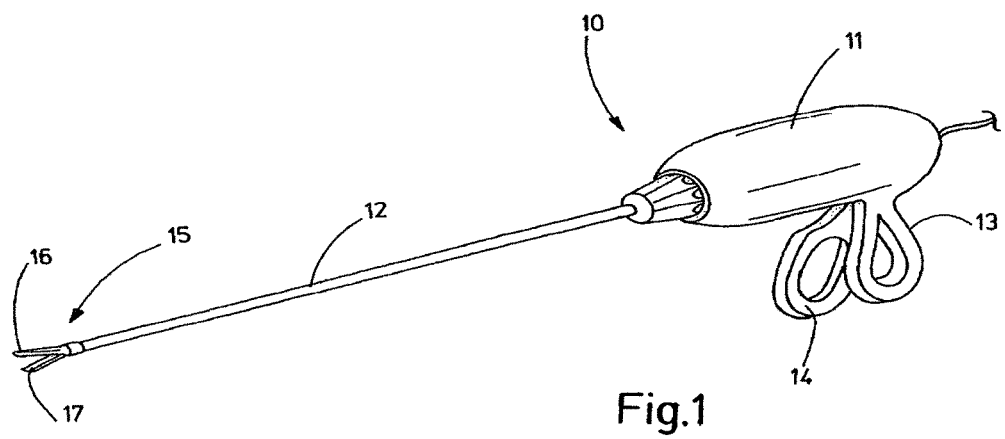
FIG. 1 shows the instrument according to the invention in a perspective schematic diagram.

FIG. 1 illustrates a surgical instrument 10, which is equipped for sealing vessels in open surgery. The instrument 10 encompasses a housing 11, from which a preferably straight shaft 12 extends away. Provision is made at the housing 11 for a handle 13, in the vicinity of which an operating lever 14 is pivotably supported. Said operating lever serves to operate a tool 15, which is attached at the distal end of the shaft 12. The instrument 10 can be embodied as disposable instrument and can thus be provided for a one-time use. The instrument 10, however, can also be embodied as an instrument, which can be sterilized and thus as a reusable instrument.

Figure 2:
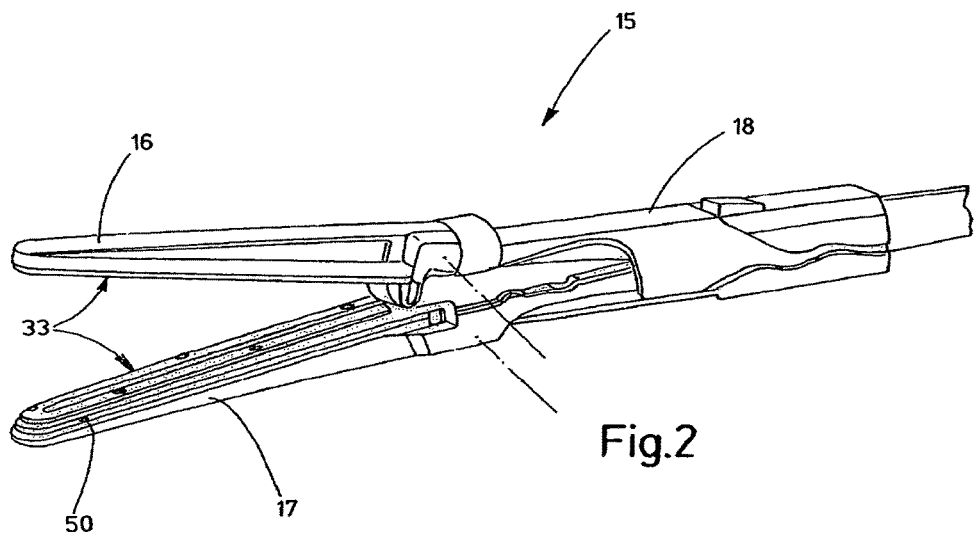
FIG. 2 shows the tool, comprising two branches, which is held at the distal end of the instrument, in schematic perspective illustration.

The distinctive feature of the instrument 10 lies in the embodiment of the tool 15, which is illustrated separately in FIG. 2. The tool 15 encompasses two branches, 16, 17, at least one of which, in the instant exemplary embodiment both, are movably supported on a base part 18. The base part 18 can consist of plastic, ceramic, composite material or also of metal, for example. In FIG. 3, the base part 18 is illustrated separately. It encompasses a support section 19 and an appendage 20, which extends away therefrom and which is inserted into the distal end of the shaft 12 and which is locked in place therein by means of a latch 21. Two bushings 22, 23, which are parallel to one another, open towards different shoulders, substantially cylindrical and which are furthermore open towards the distal end of the base part 18, are embodied in the support section 19. Provision can be made between the two bushings 22, 23 for a slit 24, through which a blade for severing coagulated tissue, for example sealed vessels, can be pushed.

The appendage 20, which embodied so as to be hollow on the inside, can encompass corrugated grooves 25 on both of its two shoulders for accommodating an electrical line, by means of which the electrode units 33 of the branches 16, 17 are supplied with voltage or current.

The branches 16, 17 in each case encompass a branch support 26, as can be seen from FIG. 4. Said branch support can consist of plastic or metal. It is embodied as a two-armed lever and encompasses a tool part 27 as well as an operating part 28. Between them, a support section 29, which fits into the support bushings 22 or 23, is arranged. The support section 29 is embodied so as to be substantially cylindrical. At a front surface, it merges seamlessly into the flat shoulder of the operating part 28, which is arranged eccentrically. In addition, the support section 29 is connected to the tool part 27 along a strip-shaped or segment-shaped area, respectively, of its cylinder jacket. A safe and resilient pivotably movable support of the branch support 26 is made possible in this manner at the base part 18.

An operating journal 30, which projects through a lateral window 31 into the interior of the appendage 20, is held at the end of the operating part 28. From there, a traction/thrust means, which acts on the operating journal 30, can lead longitudinally through the shaft 12 into the housing 11, so as to be able to move the branch support 26 by operating the operating lever 14.

The tool part 27 encompasses an accommodating surface 32 for accommodating an electrode unit 33, which can be seen from FIGS. 5 and 6. The electrode unit 33 consists of a plastic body 34 and of a sheet metal part 35. The sheet metal part 35 is illustrated separately once again in FIGS. 7 to 12.

The sheet metal part 35 forms the electrode for introducing electrical current into a biological tissue. It encompasses a preferably substantially flat tissue contact surface 36, which can be interrupted in the center by means of a longitudinal slit 37. Longitudinally pronounced flat sections of the tissue contact surface 36 extend on both sides of the longitudinal slit 37. The electrode unit 33 can be embodied so as to be completely straight, or, as can be seen from the figures, so as to be slightly curved, so as to follow a curvature of the tool part 27. In the latter case, the longitudinal slit 37 is also curved accordingly, so that the elongated sections of the tissue contact surface 36 in each case encompass a substantially constant width on both sides, as can be seen from FIG. 9.

The tissue contact surface 36 encompasses two long edges 38, 39, which are located opposite one another and from which strip sections 40, 41 extend away at an angle. The edges 38, 39 thereby preferably form rounded transitions. The strip sections 40, 41 of the tissue contact surface 36 are preferably arranged so as to be substantially parallel to one another. More preferably, they are provided with openings 42 along their entire length, which, as can be seen from FIG. 7, can be embodied as slits 43, for example. These slits 43 are separated from one another by means of webs 44, which are preferably at least as long as they are wide. The length is thereby understood in a direction vertically to the tissue contact surface 36. This direction is marked in FIG. 7 by means of an arrow X. The width is understood so as to be parallel to the longitudinal slit 37. This direction is marked in FIG. 7 by means of an arrow Y. Also in longitudinal direction, that is, in the direction of the arrow Y, the slits 43 encompass dimensions, which are preferably significantly larger than their dimensions measured vertically thereto in X-direction.

As can be seen from the exemplary embodiments of FIGS. 11 and 12, the strip sections 40, 41 can encompass different shapes. The embodiment of the strip sections is shown in an exemplary manner at the strip section 40 and can also apply for the strip section 41. The strip section 40 encompasses a substantially rectangular basic shape, which extends away from the edge 38. This basic shape is illustrated in FIGS. 11 and 12 by means of a dashed line 56. The strip section 40 can encompass slits 43 and openings 42 as described above and as illustrated in FIGS. 7 and 8. In addition or in the alternative, the strip section 40 can encompass openings 42a and slits 43a, which encompass a shape, which extends away from the edge 38 of the tissue contact surface 36 and which is open towards the bottom in FIGS. 11 and 12. The slits 43a are separated by means of webs 44, the above description of which applies. The openings 42 and 42a are designed in such a manner that they encompass holding means in the form of recesses 57 or undercuts 57, so that the plastic body 34 can be connected to the sheet metal part 35 by means of a positive connection. To ensure this, the webs 44 can also extend in Z-direction in sections (FIG. 12). As is shown in FIG. 11, it is also possible for a web 44a to encompass an area, which is embodied so as to be rotated about its own axis. In addition, different embodiments of the webs 44, 44a, of the openings 42, 42a and of the slits 43, 43a, which serve the purpose of forming a positive connection between the plastic body 34 and the sheet metal part 35, are possible.

Recesses 45, 46 are furthermore embodied in the tissue contact surface 36, for example in the shape of round holes.

At the distal rounded end 47, the sheet metal part 35 preferably does not encompass a strip section. As required, however, sections, which are bent away from the tissue contact surface 36 beyond a rounded edge, can also be present here. At the opposite proximal end 48, a connecting lug 49 can be embodied at an angled section, so as to fasten a connection line by means of material engagement or in a positive manner, for example by means of soldering, welding or crimping.

Figure 6A:
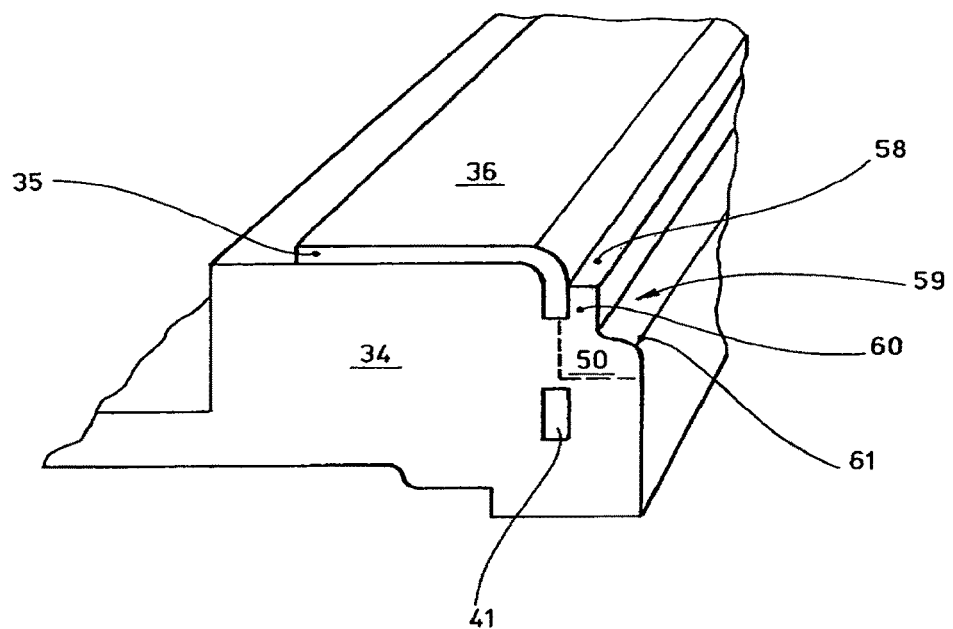
FIG. 6a shows the shoulder of the electrode unit according to FIG. 6 in enlarged, sectional illustration.

As is shown in FIG. 6, the plastic body 34 fills the gap between the strip sections 40, 41. In addition, the plastic body 34 permeates the slits 43, 43a or other openings 42, 42a, which are embodied in the strip sections 40, 41. On the outer sides of the strip sections 40, 41, the plastic body 34 forms an insulating area, for example an insulating step or shoulder 50, which creates a distance between the tissue contact surface 36 and surrounding tissue, which is not to be subjected to treatment. The shoulder 50 encompasses a substantially rectangular cross section comprising a recess 59, which is arranged on the outer side. In FIG. 6a, the cross section of the shoulder 50 is suggested by means of dashed lines. In the direction of the tissue contact surface 36, the shoulder 50 encompasses an attachment 60, which runs on the outside along the tissue contact surface 36 and which seals with a surface 58, which is placed lower as compared to the tissue contact surface 36. The tissue contact surface 36 is limited by means of this attachment 60 and the area of the tissue, through which current flows and which is seized between the branches, is determined. In addition, this attachment 60 forms a protection for the tissue against the tissue contact surface 36 and considerably prevents or reduces, respectively, thermal changes to the tissue, which is located in the area of the shoulder 50, in response to tissue sealing. The recess 59 of the shoulder 50 comprises a concavely rounded section, so that the shoulder encompasses a convexly curved area 61. In response to the closing of the branches, the tissue is held securely by means of the rounded convexly curved area 61, without damaging the tissue thereby. So as so ensure this, the attachment 60 can also encompass a rounded outer area. The shoulder 50 can encompass a width and a width and a height of between 0.1 mm and 3 mm, preferably 0.5 mm. The coagulation effect can thus be limited securely to the tissue, which is seized and compressed between the branches 16, 17. The tissue, which is seized between the shoulders 50 next to the tissue contact surfaces 36, is clamped less or not at all. The above-described areas of the shoulder 50, which are embodied so as to be rounded, can also comprise other shapes, for example angled areas. The shoulder 50 is embodied so as to protect the tissue.

The plastic body 34 furthermore extends through the recesses 45, 46 and thus forms the holding means 51, 52 (FIG. 5), which project beyond the tissue contact surface 36 and which serve the purpose of securely holding tissue, which is seized between the tissue contact surfaces 36, even if it shrinks due to the coagulation and drying. The holding means 51, 52 can furthermore act as spacers, so as to prevent a metallic contacting of the tissue contact surfaces 36 of the electrode units 33 of the two branches 16, 17 and thus an electrical short-circuit.

Centrally in the longitudinal slit 37, the plastic body 34 encompasses a blade guide groove 55. The latter is preferably considerably narrower than the longitudinal slit 37. A blade, which runs in the blade guide groove 55, is thus electrically insulated against the sheet metal part 35.

In addition to the holding means 51, 52, provision can be made at the electrode unit 33 for spacers 53, 54, which are formed by means of projections of the plastic body 34, which start at the shoulder 50, for example, and which project beyond the tissue contact surface 36. In the exemplary embodiment according to FIG. 5, these spacers 53, 54 are arranged at the distal end 47 of the electrode unit 33. In the case of other embodiments, spacers 53, 54 can be arranged at other suitable locations of the electrode unit 33 and can also form means for holding the tissue.

The instrument 10 described in this respect works as follows:

The instrument 10 is initially connected to an energized device or generator, respectively, which is not illustrated in detail, via its connecting cable. The user can then seize biological tissue, for example vessels or vessel bundles, between the tissue contact surfaces 36 of the branches 16, 17 of the tool 15 and can clamp it by operating the operating lever 14. By operating a switch, which is not illustrated in detail, the user can now apply an electrical voltage, for example a HF voltage, to the tissue contact surfaces 36 of the electrode units 33 of the two branches 16, 17, whereby electricity flows through the clamped vessel. A coagulation and fusion of vessel walls, which are located opposite to one another, can be attained through this. In the case of several embodiments, a blade can be also present. Said blade can be activated, wherein it is pushed ahead in distal direction in the blade guide groove 55 and thereby severs the vessel, which was coagulated and sealed in the meantime.

Biological tissue located outside of the branches 16, 17 of the tool 15 is thereby barely influenced or not influenced at all by the internal electrical thermal process during this process, because surrounding tissue is kept away from the tissue contact surfaces 36 and because the shoulder 50 of the plastic body 34 as well as the plastic body 34 itself and the branch supports 26 act as electrical and/or thermal insulators.

After being used, the instrument 10 can be disposed of or recycled. It is also possible to only sterilize parts of or the entire instrument 10.

The surgical instrument 10 according to the invention is suitable in particular for sealing tissue. It comprises a tool 15, which encompasses at least one branch 16 comprising an electrode unit 33, which consists of a sheet metal part 35, which is preferably embodied as stamped-bent part and is anchored in a positive manner in a plastic body 34, which is preferably embodied as injection molded part. The parts, in particular the strip sections 40, 41, which extend into the plastic body 34, encompass openings, which encompass generously dimensioned openings 42, through which the plastic body 34 extends. Not only a positive anchoring of the sheet metal part 35 in the plastic body 34 is attained, but a minimizing of the heat introduction in the edge area of the plastic body 34 is attained at the same time. The thermal capacity of the sheet metal part 35 as well as the thermal conductivity of the plastic body 34 is low, so that consistently positive coagulation results are reached even after repeated use in short succession, regardless of the initial temperature of the tissue contact surfaces 36.

LIST OF REFERENCE NUMERALS 10 instrument
11 housing
12 shaft
13 handle
14 operating lever
15 tool
16 first branch
17 second branch
18 base part
19 support section of 18
20 appendage
21 latch
22 support bushing for branch 16
23 support bushing for branch 17
24 slit
25 groove for tensile support of the electrical line
26 branch support
27 tool part
28 operating part
29 support section
30 operating journal
31 window
32 accommodating surface
33 electrode unit
34 plastic body
35 sheet metal part
36 tissue contact surface
37 longitudinal slit
38, 39 edges of the tissue contact surface 36
40, 41 strip sections
42, 42a openings
43, 43a slits
44, 44a webs
45, 46 recesses
47 distal end
48 proximal end
49 connecting lug
50 step, shoulder
51, 52 holding means, spacing means
53, 54 distal spacers
55 blade guide groove
56 rectangular basic shape of 40, 41
57 recess, undercut
58 surface of 50
59 recess of 50
60 attachment of 50
61 curved area of 50

What is claimed is:

1. A surgical instrument comprising:
   a tool including at least one branch comprising a branch support and a prefabricated electrode unit connected to the branch support,
   wherein the prefabricated electrode unit comprises a sheet metal part and a one-piece unitary plastic body; and wherein the sheet metal part defines:
  a tissue contact surface comprising two long edges, which are located opposite one another,
  strip sections having inner and outer facing surfaces, wherein the strip sections are angled away from the two long edges and extend away from the two long edges, and
  openings provided in the strip sections wherein the openings extend between the inner and outer facing surfaces; and
wherein the one-piece unitary plastic body fills a space, which is embodied between the strip sections,
wherein the one-piece unitary plastic body fills the openings in the strip sections, contacts both the inner and outer facing surfaces of the strip sections such that the strip sections are embedded within the one-piece unitary plastic body so as to anchor the sheet metal part in the one-piece unitary plastic body, and forms an insulating shoulder next to the tissue contact surface,
wherein the tissue contact surface is interrupted by a longitudinal slit, wherein the plastic body defines a blade guide groove in an aligned arrangement to the longitudinal slit,
wherein the longitudinal slit is wider than the blade guide groove,
wherein the tissue contact surface defines through-openings, through which the one-piece unitary plastic body extends so as to form tissue holding protrusions that extend beyond the tissue contact surface.

2. The instrument according to claim 1, wherein the openings are defined at least in part by webs and wherein a surface area of the openings is larger than a surface area of the webs.

3. The instrument according to claim 1 wherein a ratio of the surface area of the openings to the surface areas of the webs is between 3 to 1 and 20 to 1, preferably 10 to 1.

4. The instrument according to claim 1 wherein the openings are slits.

5. The instrument according to claim 1 wherein the sheet metal part is a shaped or bent sheet metal part.

6. The instrument according to claim 1, wherein the tissue holding protrusions are offset on both sides of the longitudinal slit.

7. The instrument according to claim 1, wherein the at least one branch includes first and second branches and the tissue holding protrusions of the first branch are arranged so as to be offset from tissue holding protrusions of the second branch.

8. The instrument according to claim 1, wherein each of the tissue holding protrusions has a surface area, wherein the surface area of each of the tissue holding protrusions ranges from between 0.5 mm$^2$ and 7 mm$^2$.

9. The instrument according to claim 8, wherein each of the tissue holding protrusions is embodied so as to assume a surface area of 0.75 mm$^2$.

10. The instrument according to claim 1 wherein spacers are arranged at an edge of the tissue contact surface.

11. A method for constructing a surgical instrument comprising:
  constructing a tool including at least one branch comprising a branch support and an electrode unit,
  constructing the electrode unit by combining a sheet metal part and a one-piece unitary plastic body so as to anchor the sheet metal part in the one-piece unitary plastic body; and
  wherein the sheet metal part defines:
    a tissue contact surface comprising two long edges, which are located opposite one another,
    strip sections having inner and outer facing surfaces, wherein the strip sections are angled away from the two long edges and extend away from the two long edges, and
    openings provided in the strip sections wherein the openings extend between the inner and outer facing surfaces; and
  wherein the one-piece unitary plastic body fills a space, which is embodied between the strip sections, and
  wherein the one-piece unitary plastic body fills the openings, contacts both the inner and outer facing surfaces of the strip sections such that the strip sections are embedded within the one-piece unitary plastic body so as to anchor the sheet metal part in the one-piece unitary plastic body, and forms an insulating shoulder next to the tissue contact surface,
  wherein constructing the electrode unit comprises interrupting the tissue contact surface with a longitudinal slit,
  wherein the one-piece unitary plastic body defines a blade guide groove in an aligned arrangement to the longitudinal slit,
  wherein the longitudinal slit is wider than the blade guide groove, and
  wherein the tissue contact surface defines through-openings, through which the one-piece unitary plastic body extends so as to form tissue holding protrusions that extend beyond the tissue contact surface; and
  attaching the electrode unit to the branch support.

12. The method according to claim 11, wherein constructing the electrode unit comprises defining the openings at least in part by webs such that a surface area of the openings is larger than a surface area of the webs.

* * * * *